United States Patent [19]
Lazo et al.

[11] Patent Number: 5,952,294
[45] Date of Patent: Sep. 14, 1999

[54] PEPTIDYL PRODRUGS AND METHODS OF MAKING AND USING THE SAME

[75] Inventors: John S. Lazo; Peter Wipf, both of Pittsburgh, Pa.

[73] Assignee: University of Pittsburgh of the Commonwealth System of Higher Education, Pittsburgh, Pa.

[21] Appl. No.: 08/690,013

[22] Filed: Jul. 31, 1996

[51] Int. Cl.$^6$ .......................... A61K 38/03; A61K 39/385; C07K 5/00
[52] U.S. Cl. .................. 514/2; 514/15; 514/18; 514/19; 424/185.1; 424/193.1; 424/457; 536/23.1
[58] Field of Search ..................... 514/15, 2, 18, 514/19; 424/185.1, 193.1, 457; 536/23.1

[56] References Cited

U.S. PATENT DOCUMENTS

| | | | |
|---|---|---|---|
| 3,975,367 | 8/1976 | Gish et al. | 260/112.5 |
| 3,991,045 | 11/1976 | Ishida et al. | 536/23 |
| 4,055,716 | 10/1977 | Ishida et al. | 536/23 |
| 4,097,665 | 6/1978 | Ishida et al. | 536/23 |
| 4,145,414 | 3/1979 | Kelly et al. | 424/180 |
| 4,367,332 | 1/1983 | Nishimura et al. | 536/23 |
| 4,745,161 | 5/1988 | Saudek et al. | 525/420 |

OTHER PUBLICATIONS

Wipf et al., Biorg. & Med. Chem. Lett. vol. 1 No. 12 pp. 745–750 (1991).

Balajthy et al., J. Med. Chem. (1992) vol. 35 pp. 3344–3349.

*Primary Examiner*—Bennett Celsa
*Attorney, Agent, or Firm*—Diane R. Meyers; Arnold B. Silverman; Eckert Seamans Cherin & Mellott, LLC

[57] ABSTRACT

Peptidyl prodrugs of therapeutic agents having an activating function are disclosed. These therapeutic agents having activating functions include those having an amino, thiol, or hydroxyl function. Methods of making and using these prodrugs are also disclosed.

14 Claims, 10 Drawing Sheets

PEPTIDYL PRODRUGS AND METHODS OF MAKING AND USING THE SAME

BACKGROUND OF THE INVENTION

1. Field of the Invention

The present invention relates to biologically protected peptidyl prodrugs generally useful in the treatment of proliferative disorders and other illnesses. These prodrugs represent a novel form of drug delivery that extends the biologically active life of many therapeutic formulations. The present invention also relates to methods of making and using these prodrugs.

2. Background of the Invention

Many therapeutic agents are limited in their use because they have an abbreviated pharmacological life. The pharmacological effect of a drug is related to the drug concentration at its site of action and the duration of drug exposure. There is a further relationship between the concentration of a drug at its site of action and the drug concentration in the systemic circulation. Drugs that can quickly metabolize or become inactivated are rapidly removed from the system circulation and therefore often require high doses and/or frequent administration to achieve effective systemic levels and the desired pharmacological activity in the body. High doses of drugs and frequent drug treatments can be costly, dangerous and impractical. Sustained-release pharmaceutical preparations reduce these problems while affording equivalent biological activity.

The present invention is generally directed to various prodrugs useful in the treatment of, among other illnesses, leukemia. The term "prodrug" as used herein, and as will be understood by one skilled in the art, refers to a biologically inactive chemical compound that is converted into a biologically active agent within the body. The prodrugs of the present invention lack pharmacological activity until they are spontaneously activated in the body to form biologically active drug forms. The activated prodrugs of the present invention generally show the same efficacy in the body as the parent compounds, but provide the added advantage of having a longer active life within the body.

The prodrug concept is of particular interest for those drugs that undergo rapid metabolism in the body. An example of one such drug is ara-C, which is also known by the names cytosine arabinoside, cytarabine and 1-(β-D-arabinofuranosyl) cytosine. Ara-C is known to be an important and effective antimetabolite for use in the therapy of acute non-lymphocytic leukemia in adults and children, acute lymphocytic leukemia and the blast phase of chronic myelocytic leukemia. It is also used in the prophylaxis and treatment of meningeal leukemia and for non-Hodgkin lymphoma in both adults and children.

Ara-C is an analogue of the pyrimidine nucleosides cytidine and deoxycytidine, with an arabinose sugar moiety replacing ribose or deoxyribose. Ara-C kills cells in the DNA synthetic phase (S-phase) of the cycle by an active process called apoptosis, and functions by inhibiting DNA polymerase, the enzyme that catalyzes the formation of DNA. To function in this capacity, the drug must be activated by pyrimidine nucleoside kinases that first promote formation of the nucleotide ara-cytosine monophosphate (ara-CMP) and then convert ara-CMP to the diphosphate and triphosphate nucleotides ara-cytosine diphosphate (ara-CDP) and ara-cytosine triphosphate (ara-CTP). Accumulation of ara-CTP causes potent inhibition of DNA synthesis in many cells. Inhibition of DNA chain elongation is effected when ara-C is incorporated at the terminal position of a growing DNA chain. There is also evidence that ara-C incorporated into DNA slows DNA template function. Cell death occurs when ara-C causes continuous inhibition of DNA synthesis for a duration of at least one cell cycle, so that cells are exposed in the S-phase. The mean cell cycle time in human acute myelocytic leukemia is one to two days.

Accumulation of sufficient ara-CTP to effectively inhibit DNA synthesis is impeded by the action of two enzymes—cytidine deaminase and dCMP deaminase. Ara-C is rapidly metabolized in the body by cytidine deaminase to form the nontoxic metabolite arauridine (ara-U); cytosine deaminase cleaves the primary amine from ara-C thereby rendering the drug inactive. In addition, dCMP deaminase converts ara-CMP to the inactive metabolite uracil arabinoside (ara-UMP). About 80% of a given ara-C does is excreted in the urine within 24 hours, with less that 10% appearing as cytarabine; the remainder is ara-U. Accordingly, the drug must be administered by continuous infusion that requires hospitalization or frequent administration of high doses that are sometimes associated with significant untoward effects.

Use of ara-C, and derivatives thereof, in the treatment of various illnesses is known in the art. For example, U.S. Pat. Nos. 3,991,045, 4,055,716 and 4,097,665 disclose $N^4$-acyl-1-β-D-arabinofuranosylcytosine, $N^4$-acyl-1-β-D-arabinofuranosylcytosine-5'-esters and diacylnucleosides, respectively, useful as chemotherapeutic agents in the treatment of cancer. U.S. Pat. No. 4,145,414 discloses 5'-esters of aracytadine, and methods of making the same, which show sustained release of ara-C in the body. U.S. Pat. No. 4,367,332 discloses $N^4$-alkoxycarbonylarabinofuranosyl cytosine compounds generally useful as anti-tumor agents.

None of the above patents teach or suggest the prodrugs, or methods of making and using the same, taught by the present invention. Accordingly, there remains a very real and substantial need to provide drugs which have a longer pharmacologically active life in the body. The present invention addresses this need.

SUMMARY OF THE INVENTION

The present invention is directed to prodrug formulations of therapeutic agents having an activating function. As used herein, the term "activating function," when used in describing a therapeutic agent, refers to those therapeutic agents which contain a reactive amino function, especially a primary or secondary amine, a reactive thiol function, or a reactive hydroxyl function. The prodrugs of the present invention are generally characterized as having a peptide moiety attached to the amino, thiol or hydroxyl function of the therapeutic agent. In a preferred embodiment the peptide moiety is attached to the drug via an azapeptide linkage. The present invention is further directed to methods of making and using these prodrugs.

It is an object of the present invention to provide prodrug formulations of therapeutic agents having an activating function which have an extended biologically active life.

It is a further object of the present invention to provide prodrug formulations of ara-C for use in the therapeutic treatment of illnesses.

It is another object of the present invention to provide methods for synthesizing prodrug formulations of therapeutic agents having an activating function.

It is yet another object of the present invention to provide methods for synthesizing prodrug formulations of ara-C.

It is another object of this invention to provide methods for using a therapeutically effective amount of a prodrug formulation of a therapeutic agent having an activating function in a patient.

It is a further object of this invention to provide methods of using in a patient a therapeutically effective amount of a prodrug formulation of ara-C.

It is a further object of this invention to provide prodrugs that can be controlled and/or altered so as to change the rate at which the prodrug becomes activated in a patient.

It is a further object of this invention to provide prodrugs that reduce or minimize the need for hospital infusion of certain therapeutic agents.

It is a further object of the present invention to provide prodrugs that resist or delay undesired enzymatic inactivation.

These and other objects of the invention will be more fully understood from the drawings and following description of the invention and the claims appended hereto.

DESCRIPTION OF THE PREFERRED EMBODIMENTS

Figure 1:
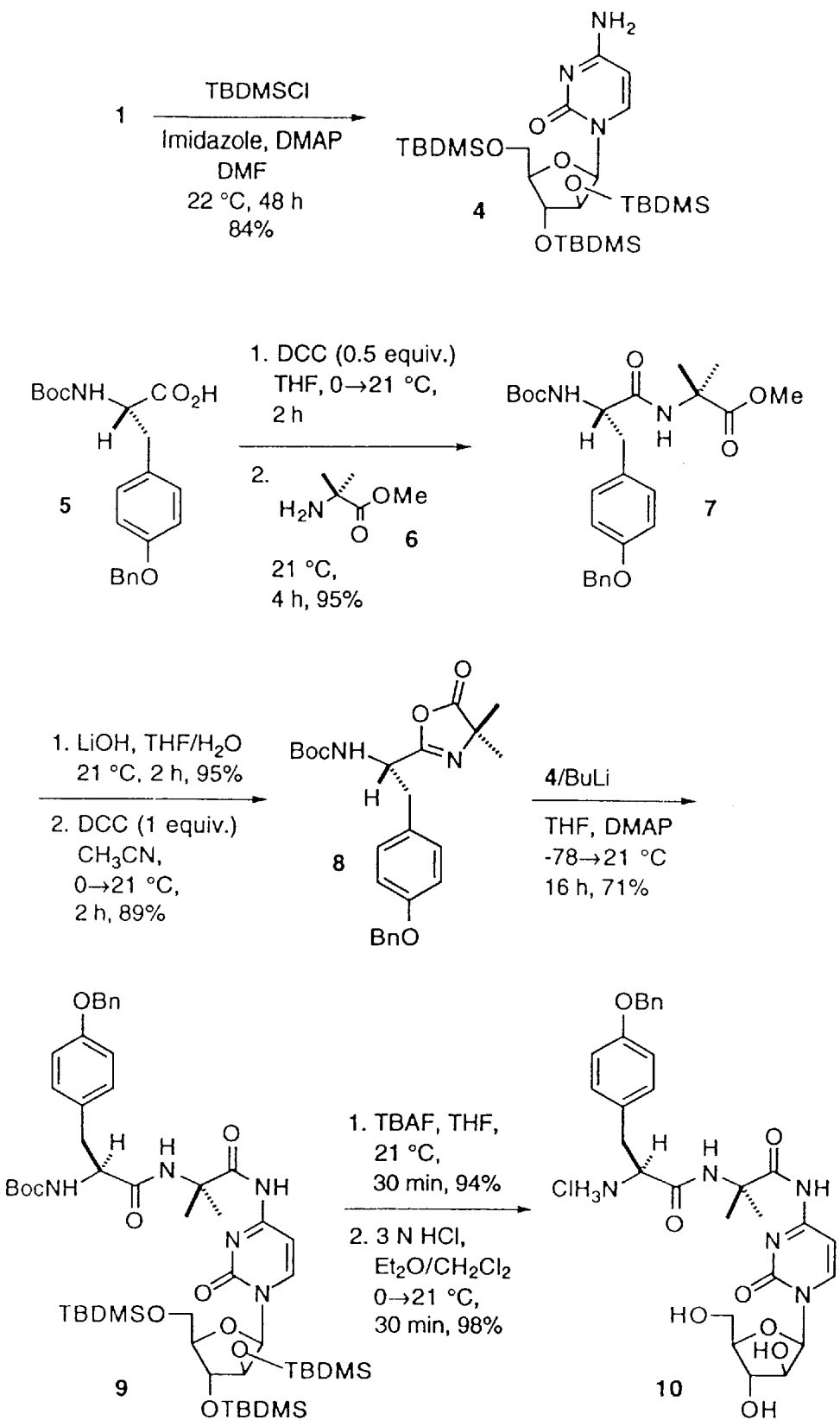
FIG. 1 shows a schematic diagram of methods for preparing a prodrug formulation according to one embodiment of the present invention.
Figure 2:
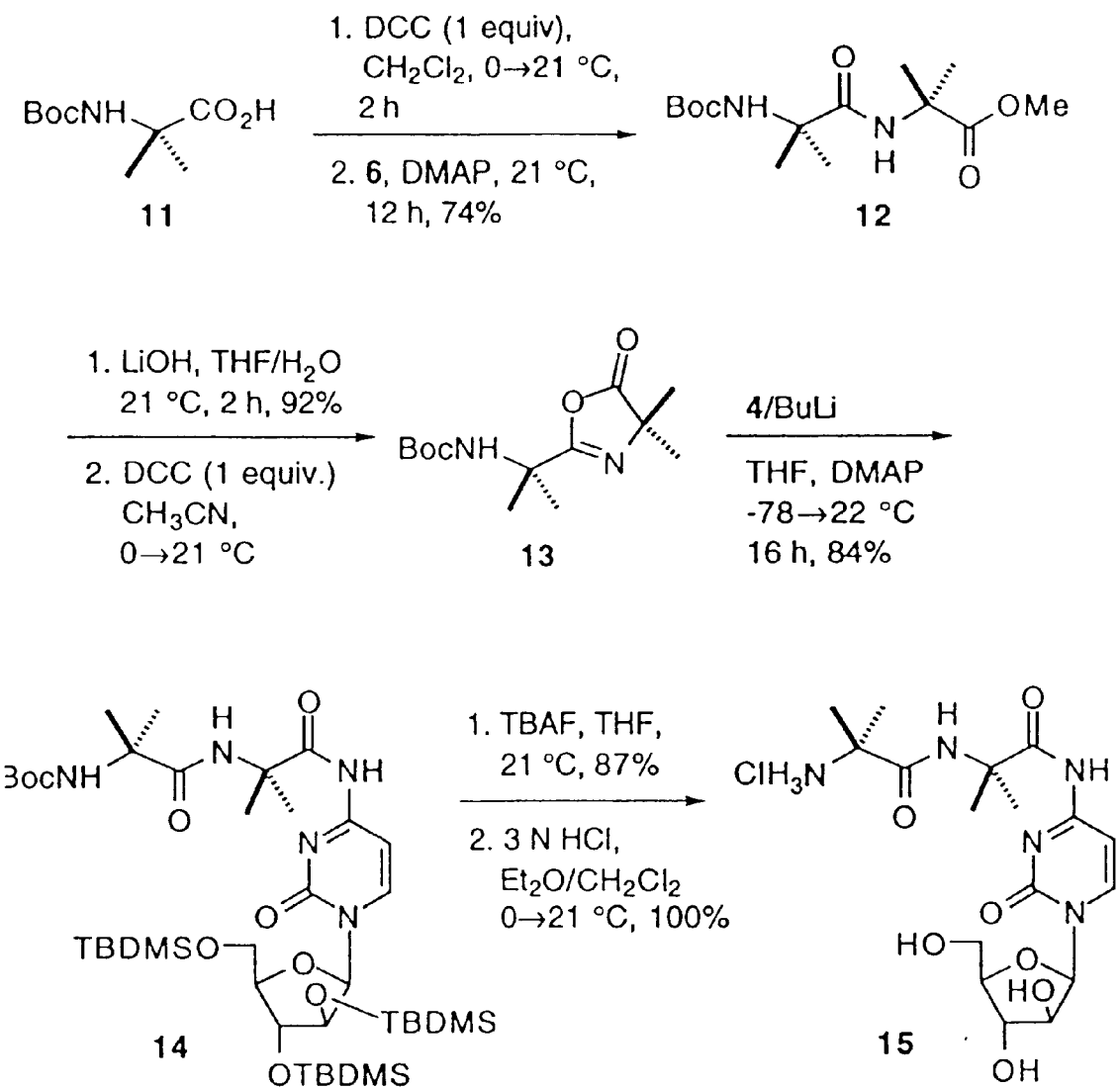
FIG. 2 shows a schematic diagram of methods for preparing a prodrug formulation according to another embodiment of the present invention.
Figure 3:
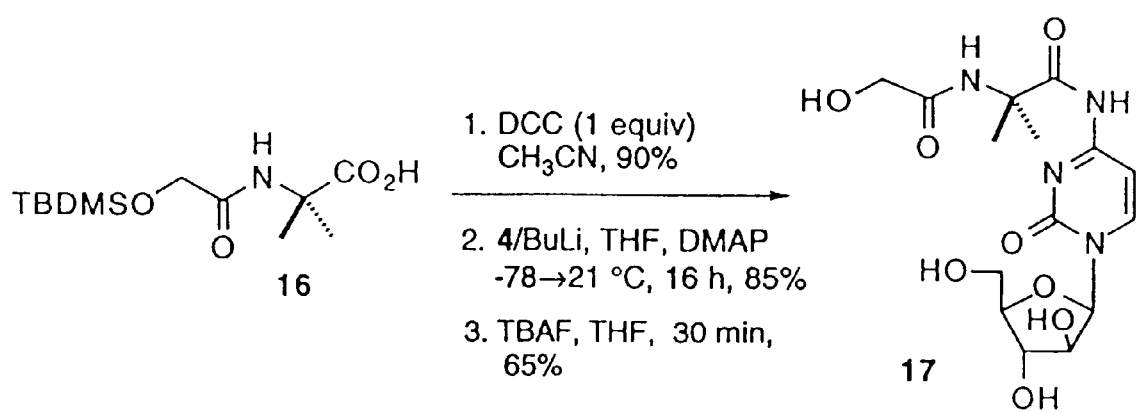
FIG. 3 shows a schematic diagram of methods for preparing a prodrug formulation according to another embodiment of the present invention.
Figure 4:
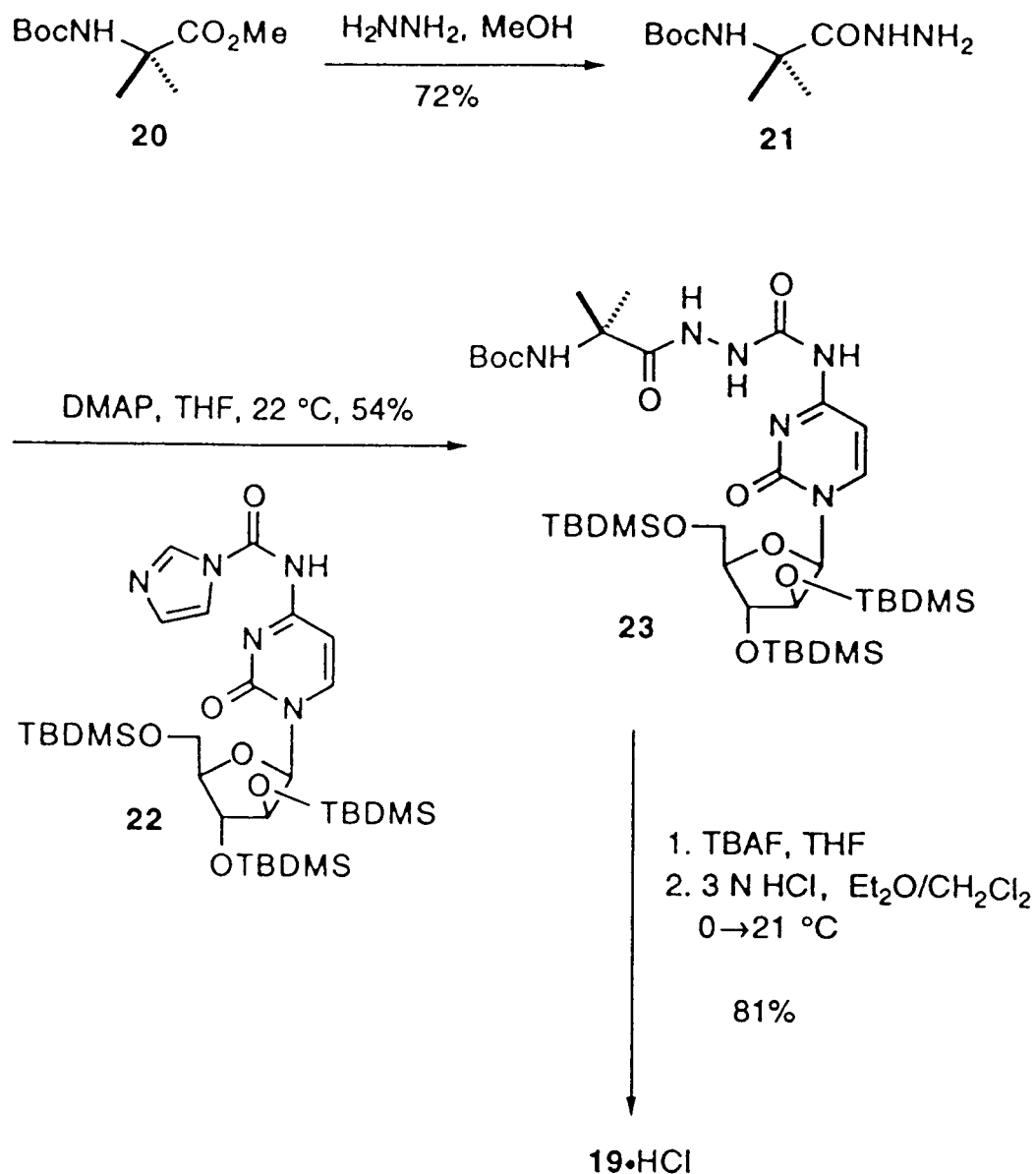
FIG. 4 shows a schematic diagram of the methods for preparing a prodrug formulation having an azapeptide linkage according to one embodiment of the present invention.

As used herein, the term "patients" refers to members of the animal kingdom including but not limited to human beings.

The present invention is directed to prodrug compositions that are generally useful in the treatment of various illnesses.

As used herein, the term "illness" refers to proliferative disorders including but not limited to cancers such as leukemia, lymphomas and neoplastic meningitis.

More specifically, the present invention is directed to a prodrug having the formula:

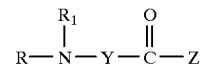

wherein R is a peptide group having between about 1 and 10 amino acids, $R^1$ is selected from the group consisting of a carbon substituent, hydrogen, nitrogen and oxygen, Y is selected from the group consisting of carbon attached to two carbon substituents, two hydrogens or one carbon substituent and one hydrogen, nitrogen attached to a carbon substituent, and NH, and Z is a therapeutic agent having an activating function. As used herein, the term "carbon substituents" refers to alkyl, allyl, aryl or other carbon based groups.

Preferably, R is a peptide group having between about 1 and 5 amino acid groups and more preferably 2 amino acid groups. In the most preferred embodiment, R is a dipeptide containing an α,α-disubstituted amino acid.

Z can be any therapeutic agent containing an activating function, including but not limited to, antiviral nucleosides, antineoplastic agents, and purine and pyrimidine nucleotide drugs. These include but are not limited to hydroxyurea, thioguanine, mitomycin C, zalcitabine, didanosine, zidovudine and stavudine. In a preferred embodiment, Z is ara-C.

As will be understood by one skilled in the art, when Y equals NH, the prodrug contains an azapeptide linkage. An azapeptide is an amino acid residue in which the α-carbon of the amino acid has been replaced with a nitrogen.

As will be understood by one skilled in the art, peptides are amino acid polymers in which the individual amino acid residues are linked together by amide, or peptide, bonds. The protected peptide groups used in the present invention can be any suitable amino acid or amino acid derived groups. As used herein, the terms "suitable peptide" and "protective peptide group" refer to any peptide or peptide analogies of the general formula

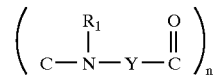

wherein $R^1$ and Y are as defined as above, and n is between 1 and 10, which is compatible with the therapeutic agents of the present invention, and which can be bonded thereto. Preferably, the peptide groups will contain between about 1 and 10 amino acids (n=1 to 10), most preferably between about 1 and 5 amino acids (n=1 to 5) and most preferably 2 amino acids (n=2). The amino acids used in the peptide groups according to the present invention can be either alpha or beta type, although the alpha type is preferred. Examples of peptide groups suitable for use in the present invention include, but are not limited to, 2-aminoisobutyric acid (Aib), isovaline, 2-methylserine, tert-leucine, 2-methylphenylalanine, 2,2-dipropylglycine and β-alanine.

Fast degradation of certain peptides by a variety of peptidases restricts the use of peptidal derivatives of active drugs. Peptides incorporating non-proteinogenic amino acids have significantly increased stabilities towards proteolytic enzymes. The rate of cleavage of the bond between peptides with α,α-disubstituted amino acids and the therapeutic agent is significantly reduced. Acylation of the therapeutic agents of the present invention with short peptides containing α,α-dialkyl amino acids is therefore most preferred. The most preferred of these compounds is 2-aminoisobutyric acid (Aib). In addition, the presence of α,α-disubstituted amino acids significantly facilitates intramolecular cyclization reactions. As will be discussed below, it is the intramoleclular cyclization reaction which causes conversion of the prodrug to the active drug form. This characteristic property can be used for the selective cleavage of the bond between peptides and the therapeutic agent.

As stated above, the prodrug concept is useful in prolonging the biologically active life of therapeutic agents which undergo a rapid metabolism in the body. An example of such therapeutic agents include those with a primary amine. An unencumbered primary amine is generally needed for biological activity. Various deaminases in the body, however, will cleave the primary amine from these therapeutic agents thereby rendering them inactive. The present inventors have discovered that protecting this primary amine with a peptide group serves to circumvent the action of the various deaminases in the body. The therapeutic agent is introduced to the body in prodrug or inactive form, which inactivation is caused by the attachment of a protective peptide group to its primary amine. This concept is equally applicable to therapeutic agents having a reactive thiol or hydroxyl function. Once in the body, the prodrug is spontaneously activated to form the active drug. Generally, the activated prodrugs are indistinguishable from the parent compounds in both structure and function. Spontaneous activation occurs by cyclization of the peptide group, which causes the peptide group to detach from the therapeutic agent thereby yielding the active therapeutic agent and a heterocycle corresponding with the peptide group. Thus, the reactive function is free and unencumbered and the therapeutic agent is capable of functioning as an active compound.

It is a feature of the present invention that the rate of release of the biologically active drug can be altered as desired. This alteration is effected by increasing or decreasing the rate of intermolecular activate function deacylation, which is determined by the chemical composition of the peptidyl moieties attached to the activating function. In the case of ara-C, the rate of release of the biologically active ara-C depends on the rate of intramolecular $N^4$-deacylation, which is determined by the chemical composition of the peptidyl moieties attached to the $N^4$ position. Accordingly, the prodrugs of the present invention function as timed release formulations whose rate of release can be adjusted by modifying the structure of the peptidyl moiety attached thereto. Generally, heterocycles of rings having 5–7 members will form preferentially, and an increase in the steric bulk of the 2-substituents on the amino acid moiety will favor the activation process.

The present invention is also directed to methods for forming the prodrugs as described above. More specifically, the present invention is directed to a method for preparing a prodrug formulation of a therapeutic agent having an activating function comprising the step of bonding a protective peptide group to the activating function of said therapeutic agent. The prodrug formulation prepared according to these methods has the general formula

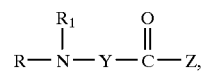

wherein R, $R^1$, Y and Z are as defined above.

Optionally, the therapeutic agent can be lithiated prior to the bonding step. Lithiation is effected by mixing the therapeutic agent with a strong base containing lithium, for example, n-BuLi in hexanes, LDA or Schwesinger base. Under certain conditions, such as when the therapeutic agent has a primary amine as its activating function, lithiation of the therapeutic agent results in an increased yield of the desired prodrug.

In addition, the presence of hydroxyl groups other than the activating function on the therapeutic agent can contribute to the low solubility of the compound in common organic solvents. Conversion of the hydroxyl groups to high solubility groups is therefore an optional step prior to the bonding step, or, if lithiation is performed, prior to the lithiating step. As used herein, the term "high solubility groups" refers to those groups attached to an oxygen molecule of the therapeutic agents of the present invention, which provide the therapeutic agents with a solubility in organic solvents higher than that achieved when the hydroxyl groups are present. The hydroxyl groups can be converted to any groups which will increase the solubility of the compound, including but not limited to tert-butyldimethylsilyl chloride (TBDMSCl), tert-butyldiphenylsilyl (TBDPSCl), other silyls, acetyl chloride groups, benzoyl chloride groups or methoxy trityl groups. If using TBDMSCl, conversion of OH groups to OTBDMS groups can be accomplished by combining TBDMSCl with the therapeutic agent in the presence of imidazole, dimethyl formamide (DMF) and dimethylamino puridine (DMAP) in a reaction which takes between about 1 to 3 days, preferably 2 days, at ambient temperature. If the activating function is a hydroxyl group, selective deprotection with a mild acid, base or fluoride anion should be affected before conversion of any other hydroxyl groups on the therapeutic agent.

If the conversion step is performed as the final step of the methods, the OH groups should be restored by removal of the protective group. Removal is effected by any means known in the art including, for example, treatment with fluoride for the silyls, catalytic hydrogenation for the benzoyl groups, and hydrolysis in dilute acid for the acetyl and methoxytrityl groups.

The step of bonding a protective peptide group to the activated function of the therapeutic agent can be accomplished by conversion of a c-terminal amino acid to an oxazolinone or activation with a coupling agent. In the case of prodrugs having the azapeptide linkage, condensation of a c-terminal hydrozide with an acyl imidazole compound is preferred. For example, the therapeutic agent can be bonded to any suitable peptide by a condensation reaction performed in the presence of a coupling agent, a polar aprotic solvent and an acylation catalyst. A suitable aprotic solvent for use in the methods of the present invention is tetrahydrofuran (THF) and a suitable acylation catalyst is DMAP. Preferably, the peptide is dissolved in dry THF and added at temperatures between about −70 and −90° C., preferably about −80° C., to a mixture containing the therapeutic agent; after addition of DMAP, the cold bath can be removed and the reaction mixture stirred at ambient temperature. The process should be effected over a time period ranging from about 12 to 20 hours, preferably about 16 hours, with stirring at ambient temperature for a period ranging from about 1 to 3 hours, preferably about 2 hours. The peptide bond can also be formed by first mixing the suitable peptide with a coupling agent before the addition of the therapeutic agent in the presence of a polar aprotic solvent and an acylation catalyst.

The present invention is further directed to a method of preparing a prodrug of ara-C comprising the steps of: (a) converting the OH groups to high solubility groups; (b) lithiating the product of step (a); (c) bonding a protective peptide group to the $N^4$ position of the product of step (b); and (d) converting said high solubility groups to OH groups.

Peptide bond formation at the $N^4$ position of ara-C is complicated by the intrinsically low nucleophilicity of this amino function; in addition, the presence of three arabinose hydroxyl groups contribute to the low solubility of the compound in common organic solvents. Conversion of the three arabinose hydroxyl groups to groups which increase the solubility of the ara-C in organic solvents is therefore performed as a first step in the above method. The hydroxyl groups can be converted to any high solubility group. Preferably, the hydroxyl groups are converted to O-tert-butyldimnethylsilyl (OTBDMS) groups. This can be accomplished by stirring ara-C in dry DMF with TBDMSCl and imidazole in the presence of DMAP.

In the next step, the product of step (a) is lithiated. This is performed by combining the tri-(tert-butyldimethylsilyl) ara-C of step (a) with sufficient quantities of a strong base containing lithium, preferably N-BuLi in hexanes.

A protective peptide group is then bonded to $N^4$ position of the product of step (b). Examples of suitable peptides for use in this step are given above; other suitable compounds include oxazolinones derived from the peptides Boc-Tyr (OBn)-Aib-OMe, Boc-Tyr(OBn)-Aib, Boc-Gly-Aib and Boc-Aib-Aib. Any means known in the art can be used to attach these groups to the $N^4$ position, such as those described above.

Conversion of the OTBDMS groups, or other high solubility groups, back to hydroxyl groups can be effected by any means known in the art. Preferably, for OTBDMS groups, this is accomplished by mixing the compound containing the protective groups with a mixture of TBAF and THF at ambient temperature for a period of about 15 minutes to 1 hour, preferably 30 minutes, and then is combining this mixture with 3 N HCl and an $ET_2O/CH_2Cl_2$ mixture at a temperature ranging from about 0° to 21° for a period of about 15 minutes to 1 hour, preferably 30 minutes.

Particular embodiments of the invention are provided in the examples below.

Figure 5:
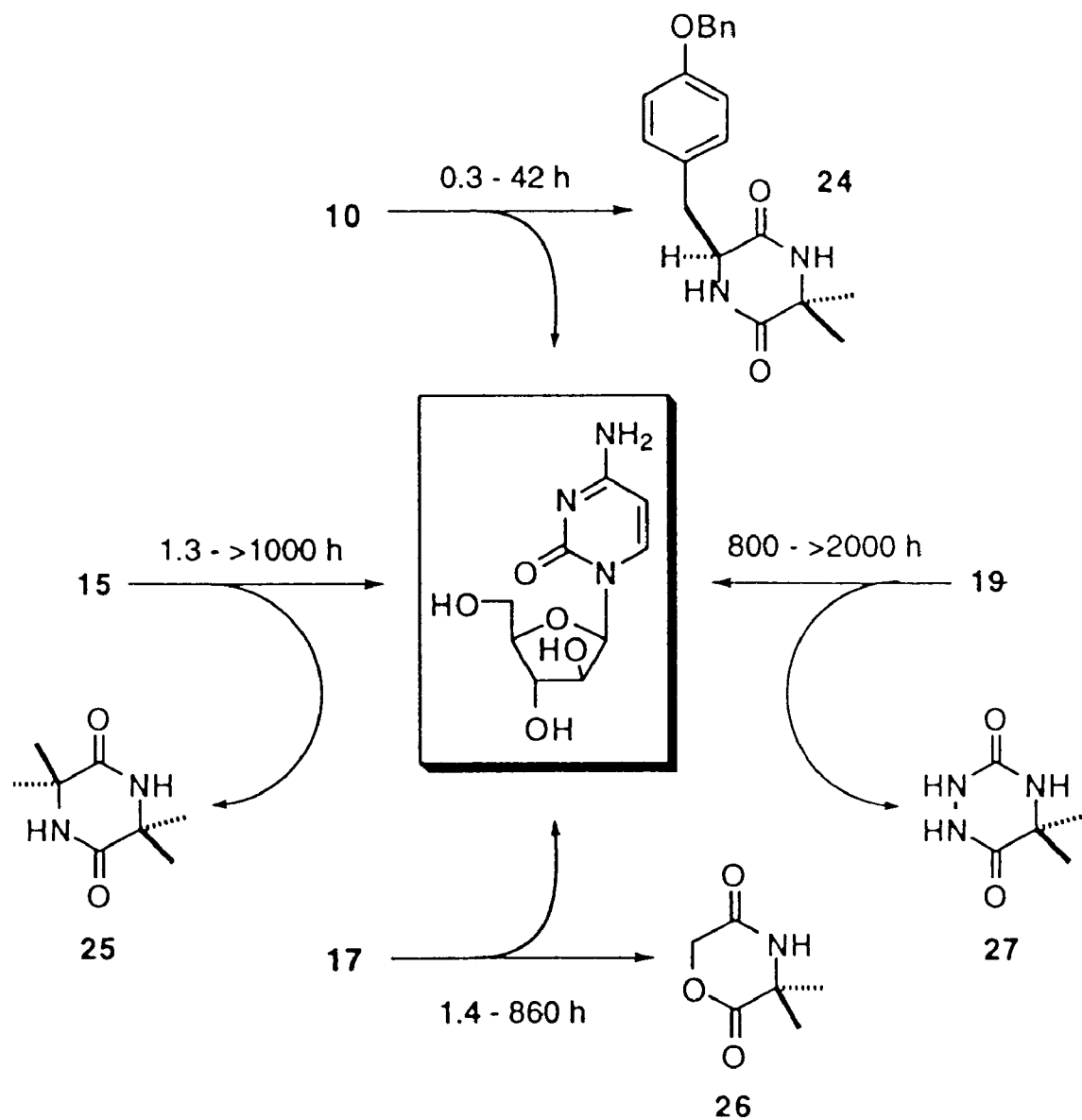
FIG. 5 shows the heterocycles which are formed upon internal cyclization of various prodrugs formulations prepared according to the present invention.

As stated previously, the protective peptide group which is bonded to the activating function of the therapeutic agent circumvents the action of various enzymes in cleaving the activating function from the therapeutic agent thereby inactivating the drug. Use of the prodrugs of the present invention having protective peptide groups avoids or substantially delays this result. According to the present invention, the protective peptide groups undergo cyclization in the body which causes the groups to detach from the host therapeutic agent. The result is a heterocycle which corresponds with the peptide group and an activated form of the therapeutic agent. FIG. 5 illustrates the heterocycle compounds which result upon intramolecular cyclization of various prodrug formulations prepared according to the methods of the present invention. The rate at which the peptide groups undergo cyclization depends on the particular peptide group which is used and is a first order process, a concept which will be familiar to one skilled in the art. The amount of time it takes for 50% of the prodrug to undergo cyclization in the body, that is—to convert from prodrug to a biologically active drug—is referred to herein as "half-life".

The present invention is further directed to a method of therapeutically treating a patient for an illness comprising the steps of: (a) employing a prodrug having the formula:

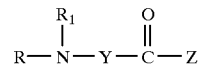

wherein R is a peptide group having between about 1 and 10 amino acid groups, $R^1$ is selected from the group consisting of a carbon substituent, hydrogen, nitrogen and oxygen, Y is selected from the group consisting of carbon attached to two carbon substituents, two hydrogens or one carbon substituent and one hydrogen, nitrogen attached to two additional carbon substituents, and NH, and Z is a therapeutic agent having an activating function; (b) incorporating said compound in a suitable pharmaceutical carrier; and (c) administering a therapeutically effective amount of said compound incorporated in said carrier to said patient.

As used herein, the term "suitable pharmaceutical carrier" refers to any pharmaceutical carrier that does not have compatibility problems with the prodrug formulation. Suitable carriers include, for example, physiologic saline, water, autologous spinal fluid and dextrose.

As used herein, the term "therapeutically effective amount" refers to that amount of a prodrug formulation incorporated in a suitable pharmaceutical carrier that is targeted to bring about a desired effect, such as inducing remission of leukemia, destroying cancer cells and the like.

A therapeutically effective amount of said compound can be administered by any means known in the art, including but not limited to, intravenously, intraparenterally, intrathecally or orally. It is well within the skill of one practicing in the art to determine what dosage, and the frequency of this dosage, which will constitute a therapeutically effective amount for each individual patient, depending on such factors as the weight of the patient, the type of illness, and the severity of such illness. It is also within the skill of one practicing in the art to select the most appropriate method of administering the prodrug formulation based upon the needs of each patient.

The prodrug compounds of the present invention can be injected subcutaneously at doses of 10 to 200 mg/m² at time periods ranging from 2 to 10 half lives with 4 half lives being the preferred schedule. Intrathecal doses of 10–60 mg/m² can be used with treatment schedules of between 2 and 10 half lives, the preferred being 4 half lives.

EXAMPLES

The following examples are intended to illustrate the invention and should not be construed as limiting the invention in any way.

Example 1

The following example provides methods for synthesizing compounds 10, 15, 17 and 19; reference numerals correspond with those in FIGS. 1 through 4.

2',3',5'-tri-(tert-butyldimethylsilyl)-ara-C (4)

About 7 g of TBDMSCl, 3.15 g of imidazole and 630 mg of DMAP were added to a solution containing 2.50 g of ara-C in 55 ml of dry DMF. The clear solution was stirred at about 22° C.; formation of the product and disappearance of the starting material were monitored by thin layer chromatography (TLC) (MeOH/CHCl$_3$ 1:9). After about 2 days, the reaction mixture was poured into 200 ml of CH$_2$Cl$_2$ and extracted with water (3×50 ml). The organic layer was dried over Na$_2$SO$_4$, evaporated to dryness and the residue chromatographed on SiO$_2$ (MeOH/CHCl$_3$ 1:19) to yield approximately 3.6 g of compound 4 and about 2.16 g of tetra-silylated product (N-silylation). The latter compound was dissolved in about 40 ml of THF and treated with 40 ml of a 10% aqueous NH$_4$OH solution. After about 4 hours of stirring at 22° C., the organic solvent was evaporated and the residue was extracted with CH$_2$Cl$_2$ (3×25 ml). The combined organic layers were dried over Na$_2$SO$_4$, evaporated to dryness and the residue chromatographed on SiO$_2$ (MeOH/CHCl$_3$ 1:19) to yield about 1.45 g of compound 4.

Boc-Tyr(OBn)-Aib-OMe (7)

A solution containing about 1.5 g of Boc-Tyr(OBn)-OH (5) in 10 ml of dry CH$_2$Cl$_2$ was treated at 0° C. with about 417 mg of DCC. The mixture was stirred at 0° C. for about 5 minutes and treated with a solution containing about 620 mg of Aib-OMe hydrochloride (6) and about 490 mg of NMM in 2 ml of dry DMF. After stirring at 22° C. for about 12 hours, the reaction mixture was extracted with a saturated aqueous solution of NH$_4$Cl. The organic layer was dried over Na$_2$SO$_4$, evaporated to dryness, and the residue chromatographed on SiO$_2$ (EtOAc/hexanes 3:7) to yield about 900 mg of compound 7.

Boc-Tyr(OBn)-Aib-2',3',5'-tri-(tert-butyldimethylsilyl-ara-C(9)

A solution containing about 260 mg of compound 7 and 91.5 mg of LiOH monohydrate in 7.5 ml of THF/H$_2$O (2:1) was stirred at 22° C. for about 3 hours. The organic solvent was evaporated and the aqueous solution was extracted with Et$_2$O (2×10 ml) and then acidified to a pH of less than 1 with 1 N HCl. The mixture was extracted again with Et$_2$O (3×10 ml) and the combined organic extracts were dried over Na$_2$SO$_4$ and evaporated to yield about 240 mg of Boc-Tyr (OBn)-Aib-OH. A solution containing about 200 mg of Boc-Tyr(OBn)-Aib-OH in 10 ml of dry CH$_3$CN was treated at 0° C. with 95 mg of DCC and stirred for about 2 hours. After filtration through florosil, the solution was evaporated to dryness. The resulting crude product (8) was dissolved in 2 ml of dry THF and added at −78° C. to a mixture of 130 mg of compound 4 and 165 μM of a 1.5 M solution of N-BuLi in hexanes in 4 ml of dry THF. After addition of about 13 mg of DMAP, the cold bath was removed and the reaction mixture stirred at 22° C. for about 2 hours. The solvent was evaporated and 4 ml of water added. After extraction with CH$_2$Cl$_2$ (3×10 ml), the combined organic layers were dried over Na$_2$SO$_4$, filtered and evaporated to dryness. The residue was purified by column chromatography on SiO$_2$ (EtOAc/hexanes, 1:1) to yield about 285 mg of compound 9.

Tyr(OBn)-Aib-ara-C hydrochloride (10)

A solution containing about 250 mg of compound 9 in 2 ml of THF was treated with about 0.93 ml of a 1 M solution of TBAF in THF, stirred for 40 minutes at 22° C., evaporated to dryness, and the residue chromatographed on SiO$_2$ (MeOH/CHCl$_3$ 1:9) to yield about 154 mg of Boc-Tyr (OBn)-Aib-ara-C. A solution containing about 89 mg of this compound in 1.45 ml of CH$_2$Cl$_2$ was treated at 0° C. with 1.5 ml of 3 N solution of HCl (gas) in Et$_2$O. The reaction mixture was stirred at 22° C. for about 30 minutes, and the precipitate filtered to yield about 81 mg of prodrug compound 10.

Boc-Aib-Aib-OMe (12)

About 200 mg of Et$_3$N and 100 mg of DMAP were added to a solution containing about 400 mg of Boc-Aib-OH (11) in 10 ml of dry CH$_2$Cl$_2$. The clear solution was cooled in an ice bath and treated with a solution of about 408 mg of DCC in 5 ml of dry CH$_2$Cl$_2$. The reaction mixture was stirred at about 22° C. for about 12 hours and the resultant slurry filtered through florosil. The filtrate was then evaporated in vacuo and the residue chromatographed on SiO$_2$ (AcOEt/hexanes 2:3) to yield about 440 mg of compound 12.

Boc-Aib-Aib-2',3',5'-tri-(tert-butyldimethylsilyl)-ara-C (14)

The procedure used to prepare compound 9 was repeated only using 300 mg of compound 12 instead of compound 7 to yield about 465 mg of compound 14.

Aib-Aib-ara-C hydrochloride (15)

The procedure used to prepare compound 10 was repeated using about 250 mg of compound 14 instead of compound 9 to yield 105 mg of prodrug compound 15.

Glc-Aib-ara-C (17)

The procedure used to prepare compound 9 was repeated using about 200 mg of compound 16 instead of compound 7 to yield about 468 mg of TBDMS-Glc-Aib-2',3',5'-tri-(tert-butyldimethylsilyl)-ara-C. The procedure used to prepare compound 10 was repeated using about 330 mg of this compound instead of compound 9 to yield about 98 mg of prodrug compound 17.

2-Boc-1'-aminoisopropyl-1,3,4-oxadiazol-5-one (18)

A solution containing about 160 mg of compound 22 in 4 ml of THF was treated at 22° C. with about 144 mg of N,N'-carbonyldiimidazole (CDI). The reaction mixture was stirred for about 3 hours. The solvent was evaporated and the residue chromatographed on SiO$_2$ (AcOEt/hexanes 2:3) to yield about 152 mg of compound 18.

Boc-Aib-NHNH$_2$ (21)

A solution containing about 570 mg of Boc-Aib-OMe (20) in about 1.5 ml of MeOH was treated at 22° C. with about 622 mg of H$_2$NNH$_2$ monohydrate. The solution was heated and stirred at 55° C. for about 24 hours, and then cooled to about 22° C. The solvent was evaporated in vacuo to yield about 410 mg of crude compound 21.

Boc-Aib-2-Azagly-2',3',5'-tri-(tert-butyldimethylsilyl)-ara-C (23)

A solution containing about 130 mg of compound 4 in 2 ml of dry THF was cooled to −78° C. and treated with about 100 microliters of a 2.5 M solution of N-BuLi in hexanes. After about 5 minutes, a solution containing about 54 mg of CDI in 2 ml of THF was added. A dry ice-acetone bath was removed after 10 minutes, and the reaction mixture was stirred for 1 hour before 96 mg of compound 21 and 13 mg of DMAP were added. After stirring for about 20 hours, the solvent was evaporated and the residue chromatographed on SiO$_2$ (AcOEt/hexanes 4:1) to yield about 58 mg of compound 4 and 55 mg of compound 23.

Aib-2-Azagly-ara-C hydrochloride (19)

The procedure used to prepare compound 10 was repeated using about 90 mg of compound 23 instead of compound 9 to yield about 34 mg of ara peptide prodrug compound 19.

Example 2

The stability of the ara-C prodrug compounds 10, 15, 17 and 19, prepared according to Example 1, in various reaction media was investigated by NMR and HPLC analyses. The $^1$H NMR studies of the cyclization process were performed on a 4 mg/ml solution of prodrug in $CD_3OD$ or $D_2O$. Sodium acetate (2 mg) or acetic acid (2 microliters) were added neat to the samples to control the pH. The spectra were collected in appropriate time intervals, and the ratio of prodrug to drug was determined by comparing the integration of the H-C (6) on the nucleoside of prodrug and ara-C.

Figure 6:
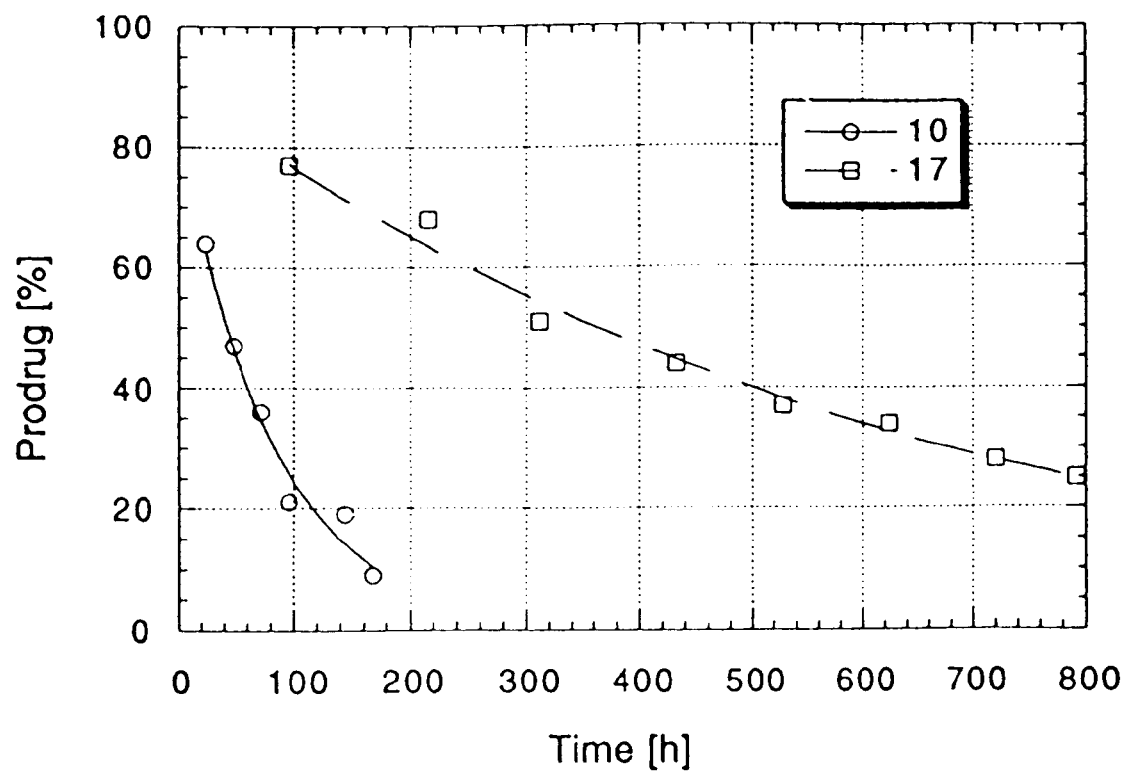
FIG. 6 is a graph illustrating release of ara-C from compounds 10 and 17 in MeOH-$d_4$ at 22° C. as monitored by $^1$H NMR, determined according to the methods of Example 2.
Figure 7:
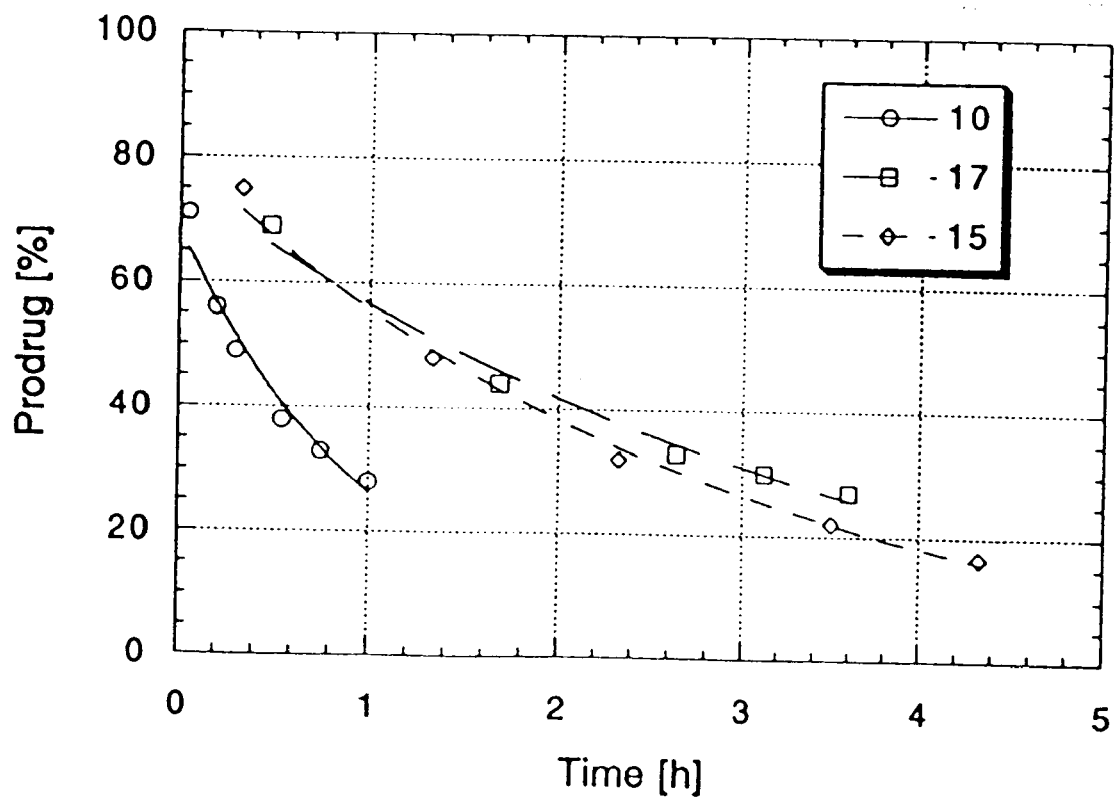
FIG. 7 is a graph illustrating release of ara-C from compounds 10, 15 and 17 in the presence of NaOAc in MeOH-$d_4$ at 22° C. as monitored by $^1$H NMR, determined according to the methods of Example 2.
Figure 8:
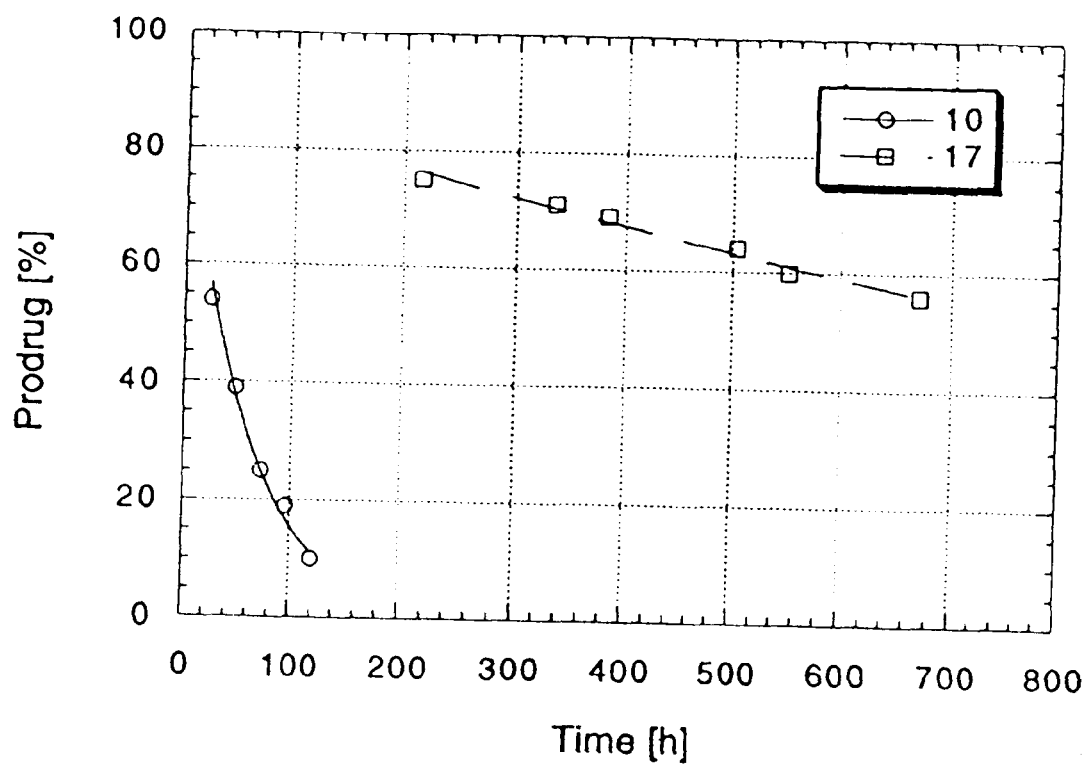
FIG. 8 is a graph illustrating release of ara-C from compounds 10 and 17 in the presence of HOAc in MeOH-$d_4$ at 22° C. as monitored by $^1$H NMR, determined according to the methods of Example 2.

HPLC studies of the cyclization process in plasma were performed on a 4 mg/ml solution of prodrug in plasma. At appropriate time intervals, 25 microliter aliquots were removed and 0.20 ml of $CH_3CN$ was added to precipitate the protein. After centrifugation, about 25 microliters of clear supernatant liquid was injected directly into the HPLC port. The HPLC analysis was performed with a C-18 reverse phase column using an $H_2O/CH_3CN$ (1:1) eluent and the UV detector was set at 250 nm. The relative concentration of ara-C was determined by the relative peak areas. It was found that the rate of release of ara-C was dependent upon the peptide structure and the pH of the medium. The disappearance of characteristic signals of the prodrugs was accompanied by the appearance of signals of ara-C and the corresponding heterocycles. Kinetic analysis showed that the drug was formed following a first order rate law. FIGS. 6 through 8 plot the percent concentration of prodrug over time. Table 1 below provides the half life (in hours) for ara-C release of prodrugs 10, 15, 17 and 19 as determined by NMR and HPLC analysis.

TABLE 1

Half-life (hours) For Release of ara-C
From Prodrugs 10, 15, 17 and 19 in Various Conditions

| | | $t_{1/2}$ | | | |
|---|---|---|---|---|---|
| Entry | Conditions | 10 | 15 | 17 | 19 |
| 1 | $CD_3OD$, 22° C. | 42 | >1000 | 360 | >2000 |
| 2 | $CD_3OD$, 22° C., NaOAc | 0.3 | 1.3 | 1.4 | 800 |
| 3 | $CD_3OD$, 22° C., HOAc | 31 | >1000 | 860 | >2000 |
| 4 | $D_2O$, 22° C. | 21 | ND | ND | ND |
| 5 | Bovine plasma, pH 7.4, 22° C. | 0.4 | 0.5 | 0.4 | >10 |
| 6 | Human plasma, pH 7.4, 22° C. | 0.3 | 0.4 | 0.3 | >10 |

ND = not determined

As can be seen from the Table, prodrug 10 was found to have the shortest half life among all of the derivatives. The process of drug release was greatly enhanced in the presence of NaOAC. In the presence of HOAc, however, the intramoleclular cyclization was only slightly accelerated, or, in compound 17 actually decelerated. The rate of cyclization of amines 10 and 15 appeared to be dependent on the concentration of free amine versus ammonium salt and should therefore be accelerated in neutral or basic environments. The presence of a bidentate proton acceptor/donor moiety appears to be especially advantageous for the intramolecular carbonyl addition. Upon change of the reaction mixture from $CD_3OD$ to $D_2O$, compound 10 cyclized about 50% faster.

In general, Compound 17 cyclized slower than compound 10. It is believed that this is a result of the lower nucleophilicity of the hydroxyl versus the amino group. In addition, compound 17 cyclized more slowly in an acidic medium than in a neutral one. While derivative 15 cyclized readily in the presence of NaOAc, its half life was extremely long in the absence of NaOAc or with an excess of HOAc. The azapeptide derivative 19 did not undergo cyclization to release the drug in neutral or acid conditions, and cyclization was extremely slow even in the presence of NaOAc.

The stability of these compounds in bovine and human plasma was determined by HPLC analysis (Entry 5 and 6 in Table 1). Compounds 10, 15 and 17 were found to cyclize readily in bovine or human plasma. In contrast, compound 19 showed good stability in plasma. No ara-C was detected after 48 hours.

Example 3

The antiproliferation activity of compounds 10, 15, 17 and 19, as compared to ara-C, was tested in an L-1210 cell line growth inhibition assay using various concentrations and continuous exposure. Cell numbers were determined 72 hours after initial drug exposure. Murine L-1210 leukemia cells were grown in suspension using Dulbecco's medium (Gibco/BRL) supplemented with 10% fetal bovine serum (FBS, HyClone), 2 micromols of L-glutamine, 100 U/ml penicillin G sodium, and 100 µg/ml streptomycin (Gibco/BRL). Cells were grown in a humidified incubator as 37° C. under an atmosphere of 95% air and 5% $CO_2$. Cells were routinely passaged at a 1:5 ratio and found to be free of mycoplasma contamination. The cell growth inhibition in nanograms per milliliter (ng/ml) for each of the compounds tested is given in Table 2 below.

TABLE 2

L-1210 Cell Growth Inhibition (ng/ml)

| Entry | Compound | $IC_{50}$ | $IC_{90}$ |
|---|---|---|---|
| 1 | 10 | 1.3 | 5 |
| 2 | 15 | 1.1 | 3.4 |
| 3 | 17 | 1.0 | 3.4 |
| 4 | 19 | 600 | 1400 |
| 5 | ara-C | 1.5 | 4.3 |

$IC_{50}$ and $IC_{90}$ refer to the concentration of compound required to inhibit cell activity by 50 and 90%, respectively. As will be appreciated by one skilled in the art, the lower the IC value, the more potent the drug.

$IC_{50}$ and $IC_{90}$ values of compounds 10, 15 and 17 were essentially identical to the ara-C control. This demonstrates that compounds 10, 15 and 17 have comparable efficacy to ara-C. The azapeptide compound, 19, was about 500 more times less toxic in this test.

Example 4

The ability of the prodrug compounds to kill human tumor cells was tested, specifically their ability to induce apoptosis in human promyelocytic leukemia HL-60 cells. These cells are known to undergo apoptosis following exposure to ara-C. The ability of the prodrugs to cause internucleosomal DNA fragmentation, a characteristic feature of apoptosis in HL-60 cells, was also investigated. The HL-60 were cultured in essentially the same manner as the L-1210 cells, only using Iscoue's modification for the medium. Internucleosomal DNA fragmentation was determined as follows. Following the indicated drug treatments, aliquots of cells (1×10$^6$) were pelleted by centrifugation at 100×g for 5 minutes, washed with PBS, solubilized with 20 microliters of lysis buffer (10 mM EDTA, 0.5% sarkosyl, 1 mg/ml proteinase K, 50 mM Tris, pH8), and incubated at 50° C. for 1 hour. After incubation, RNaseA (Boehringer Mannheim)

was added to a final concentration of 0.33 mg/ml and incubated for an additional hour at 37° C. The lysate was loaded into dry wells of a 1.8% agarose gel, the wells were sealed with low melting point agarose, and the DNA was electrophoresed using Tris-phosphate-EDTA (TPE) running buffer. After electrophoresis, the DNA was stained by immersion of the gel in water containing 1 μg/ml ethidium bromide (Sigma). The DNA was visualized and photographed using an ultraviolet transilluminator.

Figure 9:
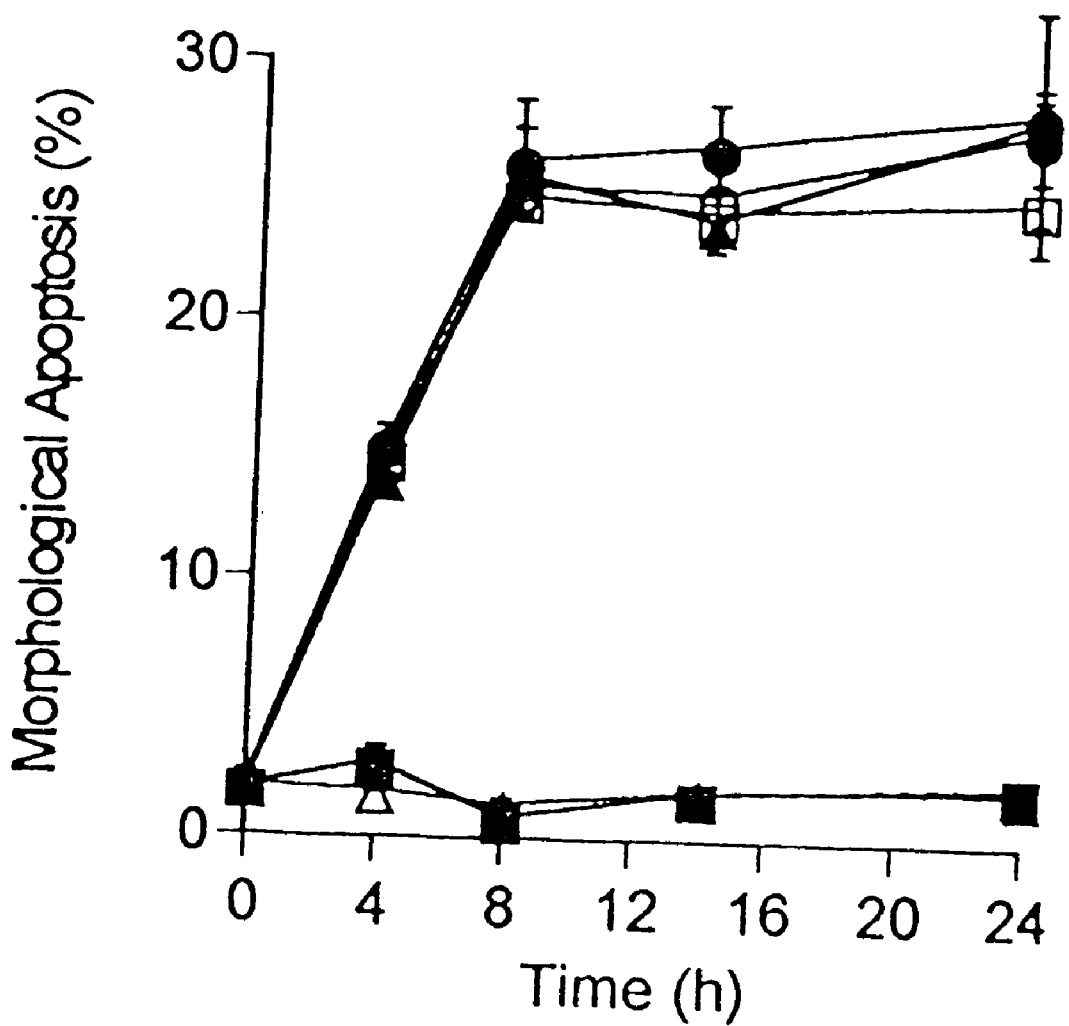
FIG. 9 is a graph plotting the percentage of human tumor cells displaying morphological evidence of active cell death, known in the art as apoptosis, over time (hours) for ara-C, compounds 10, 15, 17 and 19 and a DMSO control, determined according to the methods of Example 4.

After a 24 hours exposure to about 10 micromols of ara-C, the appearance of obvious apoptotic bodies was seen in HL-60 cells. Compounds 10, 15 and 17 produced similar results, but compound 19 did not. As can be seen in FIG. 9, no significant difference in the efficacy of the active compounds was noted, with a maximum of approximately 25% of the cells treated with ara-C, 10, 15 and 17 exhibiting a frank apoptotic morphology. The formation of apoptotic bodies occurred within a maximal halftime of 4 hours and there was no noticeable difference in the kinetics of apoptosis among ara-C, 10, 15 and 17. Compound 19 produced no obvious increase in apoptosis during the 24 hours observation period.

Figure 10:
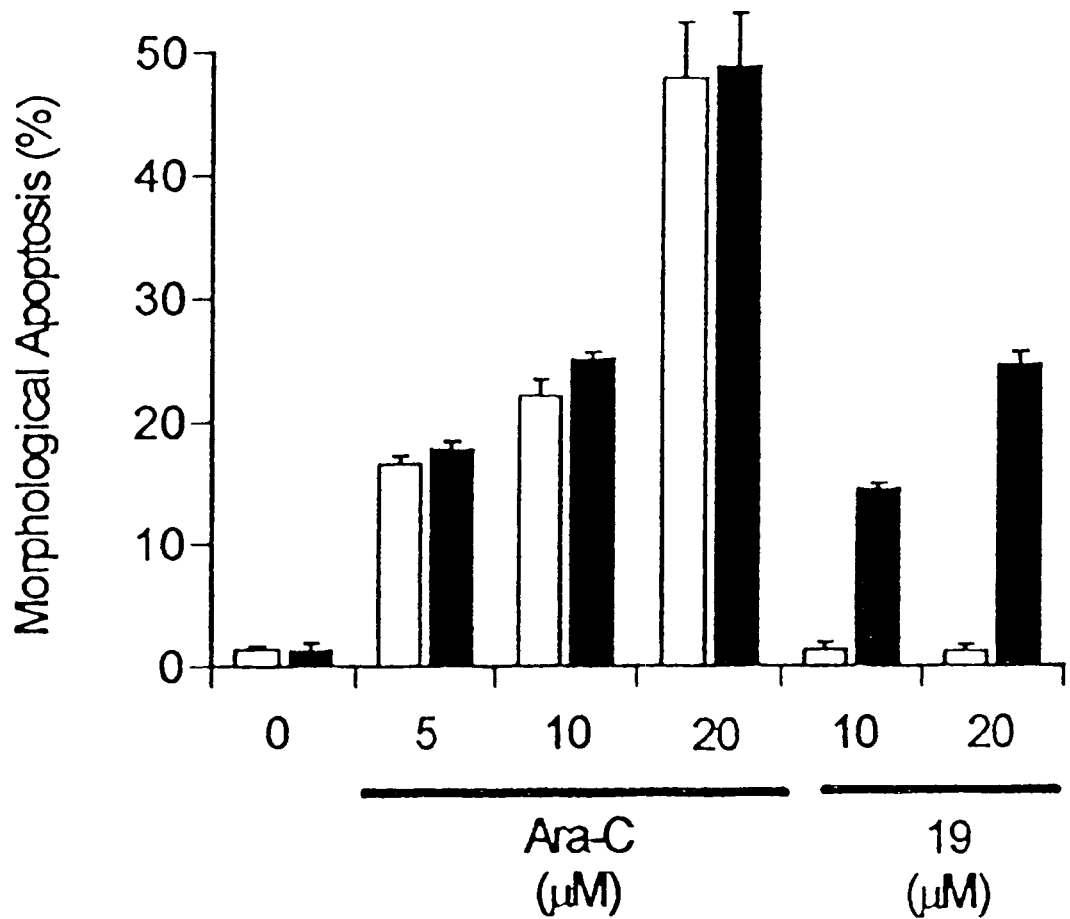
FIG. 10 is a graph plotting morphological apoptosis (%) versus concentration ($\mu$M) of preincubated ara-C and compound 19 and a DMSO control, determined according to the methods of Example 4.

DNA fragmentation of the compounds was tested. HL-60 cells treated with about 10 micromols of ara-C for 4 hours displayed internucleosomal 180–200 base pair DNA fragments. Similar DNA ladders were seen with compounds 10, 15 and 17. Because of the relatively long in vitro half life of compound 19, it was preincubated in serum-free medium for 15 days. As can be seen from FIG. 10, preincubation of compound 19 enhanced the apoptotic activity to levels that were slightly less than ara-C. In addition, DNA fragmentation was also seen with preincubated compound 19 which displayed DNA ladders similar ara-C. Thus the efficacy of preincubated compound 19 was similar to that of ara-C.

It will be appreciated that the present invention provides prodrugs of therapeutic agents, and methods of making and using the same, wherein said therapeutic agents are characterized as having an activating function including but not limited to an amino function, a thiol function or a hydroxyl function. These prodrugs circumvent enzymatic removal of the activating function from the therapeutic agent thereby functioning in a timed release manner. In addition, these prodrugs are not toxic to humans.

Whereas, particular embodiments of this invention have been described above for purposes of illustration, it will be evident to those skilled in the art that numerous variations of the details of the present invention may be made without departing from the invention as defined in the claims.

What is claimed is:

1. A spontaneously activated prodrug having the formula:

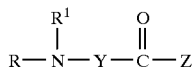

wherein R is a peptide group having between about 1 and 10 amino acids which are attached to the rest of the prodrug by its main chain carboxyl terminus; $R^1$ is selected from the group consisting of a carbon substituent and hydrogen; Y is nitrogen substituted by hydrogen or a carbon substituent; and Z is ara-C which is linked by its amino group to the carbonyl of the prodrug which allows for the spontaneous release of ara-C.

2. The prodrug of claim 1, wherein R is a peptide group having between about 1 and 5 amino acid groups.

3. The prodrug of claim 2, wherein R is a peptide group having 2 amino acid groups.

4. The prodrug of claim 3, wherein R is an α,α-disubstituted amino acid.

5. The prodrug of claim 1, wherein R is selected from the group consisting of 2-aminoisobutyric acid, isovaline, 2-methylserine, tert-leucine, 2-methylphenylalanine, 2,2-dipropylglycine and β-alanine.

6. The prodrug of claim 1, wherein R is selected from the group consisting of 2,2-dialkyl and 2,2-diaryl amino acids.

7. The prodrug of claim 1 having a half-life in a patient of between about 10 minutes and 10 days.

8. A method of therapeutically treating a patient having an illness comprising the steps of:

a) incorporating into a suitable pharmaceutical carrier a spontaneously activated prodrug having the formula:

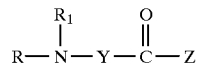

wherein R is a peptide group having between about 1 and 10 amino acids which are attached to the rest of the prodrug by its main chain carboxyl terminus; $R^1$ is selected from the group consisting of a carbon substituent and hydrogen; Y is nitrogen substituted by hydrogen or a carbon substituent; and Z is ara-C which is linked by its amino group to the carbonyl of the prodrug which allows for the spontaneous release of ara-C; and b) administering a therapeutically effective amount of said compound incorporated in said carrier to a patient; wherein said prodrug is spontaneously activated in said patient.

9. The method of claim 8 wherein said patient has an illness selected from the group consisting of leukemia, lymphoma and neoplastic meningitis.

10. The method of claim 8 wherein said carrier is selected from the group consisting of physiologic saline, dextrose, water and autologous spinal fluid.

11. The method of claim 8 including administering said compound incorporated in said carrier to a patient subcutaneously.

12. The method of claim 8, including administering said compound incorporated in said carrier to a patient intrathecally.

13. The method of claim 8, including administering said compound incorporated in said carrier to a patient intravenously.

14. A method of administering a spontaneously activated prodrug having the formula:

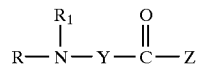

wherein R is a peptide group having between about 1 and 10 amino acids which are attached to the rest of the prodrug by its main chain carboxyl terminus; $R^1$ is selected from the group consisting of a carbon substituent and hydrogen; Y is nitrogen substituted by hydrogen or a carbon substituent; and Z is ara-C which is linked by its amino group to the carbonyl of the prodrug which allows for the spontaneous release of ara-C, comprising the step of administering said prodrug to a patient every 2 to 10 half lives.

* * * * *

UNITED STATES PATENT AND TRADEMARK OFFICE
CERTIFICATE OF CORRECTION

PATENT NO. : 5,952,294

DATED : September 14, 1999

INVENTOR(S) : Lazo, et al.

It is certified that errors appear in the above-identified patent and that said Letters Patent should be corrected as shown below:

Col. 4, line 41, the word "analogies" should read --analogue--.

Signed and Sealed this

Twenty-ninth Day of May, 2001

Attest:

NICHOLAS P. GODICI

*Attesting Officer*  *Acting Director of the United States Patent and Trademark Office*